United States Patent [19]

Clyde

[11] 4,351,905
[45] Sep. 28, 1982

[54] HORIZONTAL FERMENTER

[76] Inventor: Robert A. Clyde, Box 486, Alfred, N.Y. 14802

[21] Appl. No.: 216,310

[22] Filed: Dec. 15, 1980

[51] Int. Cl.³ .............................................. C12M 1/02
[52] U.S. Cl. .................................. 435/316; 435/313; 435/315; 435/813
[58] Field of Search ............... 435/288, 311, 312, 313, 435/314, 315, 316, 813

[56] References Cited

U.S. PATENT DOCUMENTS

| | | | |
|---|---|---|---|
| 3,878,301 | 4/1975 | Berdelle-Hilge | 435/801 X |
| 3,981,803 | 9/1976 | Coulthard | 435/801 X |
| 3,983,000 | 9/1976 | Messing et al. | 435/176 |
| 4,071,409 | 1/1978 | Messing et al. | 435/176 |
| 4,127,447 | 11/1978 | Griffith et al. | 435/176 X |
| 4,138,292 | 2/1979 | Chibata et al. | 435/178 |
| 4,149,936 | 4/1979 | Messing et al. | 435/176 |
| 4,153,510 | 5/1979 | Messing et al. | 435/176 |
| 4,206,259 | 6/1980 | Rohrbach et al. | 435/180 X |
| 4,242,450 | 12/1980 | Honda et al. | 435/288 X |

FOREIGN PATENT DOCUMENTS 615841 2/1980 Switzerland ...................... 435/288

Primary Examiner—Robert J. Warden

[57] ABSTRACT

A horizontal fermenter which allows the uninhibited growth of an organism is disclosed. The fermenter is particularly useful for producing alcohols such as ethanol from sugars such as glucose, and comprises a container for holding a selected nutrient solution. A fiber or wood substrate is included for supporting a selected organism such as Zymomonas. Also included is means for physically detaching or dislodging the organisms from the substrate.

16 Claims, 9 Drawing Figures

HORIZONTAL FERMENTER

BACKGROUND OF THE INVENTION

This invention relates to methods and apparatus for manufacturing ethanol and other alcohols from sugar solutions which may be obtained from the hydrolysis and breakdown of many agricultural and biological residues and wastes. More particularly, this invention relates to the manufacturer of such alcohols by the use of immobilized cell reactors.

In this period of critical energy shortages, the nations attention is being directed toward the development of alternate or plentiful sources of energy. Particularly, as world reserves of petroleum are depleted, new sources of carbon and hydrogen must be found to supply mankinds chemical and energy needs. While our present sources of petroleum are being rapidly depleted, it will be appreciated that in most parts of the world large quantities of biological residue materials are available which can be converted to suitable chemicals. For example, it has been estimated that the United States alone has about three hundred million dry tons a year of agricultural residues. In particular, corn stover accounts for about one-half of the total U.S. agricultural residue. At present, it has been estimated that this corn residue alone could supply all of the petro chemical needs of the United States if a conversion efficiency as low as forty percent can be obtained. But, in addition to the corn stover there are, of course, many other biological and agricultural residues including corn cobs, pine and oak bark, wheat, straw, and any and all other types of animal vegetable and plant matter. Thus, even though the percentage of conversion will vary, the primary constituents of all such plant material are well recognized as being starch, cellulose, hemicellulose and lignin. The hemicellulose and cellulose fractions can be converted into energy or chemicals by direct combustion (i.e. burning), pyrolysis or biological conversion. To date, direct combustion has been the most commonly used. But, biological conversion is much preferable because of the higher efficiency and the preservation of minerals and nutrients which can be returned to the soil. However, to be able to convert these agricultural residues by biological means it will be necessary to hydrolize the starch, cellulose or hemicellulose into monomeric sugars such as xylose, pentoses, hexoses, and galactoses. These simple sugars can then easily be converted into alcohols, acids, aldehydes or gases depending upon the type of microorganism selected for the biological conversion.

The most common way of converting various sugars such as xylose and glucose into ethanol has been by batch fermentation and continuous stirred tank fermentation (CSTF). Unfortunately, both of these techniques are slow and are quite susceptable to inhibition of growth from materials in the substrate or in the product. Typically, for example, the batch fermentation vats are drained and cleaned every two or three days and hence are out of production 25% to 30% of the time. Because of these difficulties, there is a definite need for an efficient technique of converting simple sugars such as glucose and xylose into ethanol. The simple sugars are easily obtained by hydrolyzing cellulose and hemicellulose containing materials such as corn stover and the like. For example, Dr. James Gaddy at the University of Missouri in Rolla discovered that the reaction rate of glucose fermentation to ethanol could be increased nine (9) times if the yeast was attached to ceramic Raschig Rings rather than put into the solution and run continuously. In addition, there was no washout, as the yeast stayed in the reactor. Gaddy proposed columns 12 ft. in diameter and 50 ft. high filled with Raschig Rings. No mixing is possible after inoculation. The applicant of the present invention has an application now pending in the Patent Office which describes a high area ceramic contactor which should provide even better rates than the Raschig Rings. In an experiment by the applicant in which string was used to suspend a ceramic high area contactor in a nutrient solution, it was discovered that significantly more bacterial growth adhered to the string than to the ceramic. Thus, it is seen that techniques for immobilizing various enzymes by attachment to water insoluble materials has received considerable attention recently. However, as is pointed out in volume 261, of the *Nature Magazine*, dated May 20, 1976, a logical extension of this approach of immobilizing enzymes is the immobilization of other microorganisms which are often themselves the source of enzymes. The advantage of immobilizing the microorganism itself is obvious since the time consuming procedures for enzyme extraction and purification are eliminated, and cofactors and coenzymes are readily available. Further, the cellular enzymes are often organized into the requisite metabolic pathways such that problems associated with the enzyme instability may be avoided. In addition, the use of immobilized cells avoids the problems in industrial processes of separating the product from the enzyme. Early techniques of immobilization of cells included the standard glutaraldehyde procedure and entrapment in a polyacrylamide gel. Unfortunately, use of polyacrylamide gel produces a minimum interaction between the microbial cell and the nutrients in the medium. This maximizes the probability of cell survival, but the availability of the cell to any intended nutrients is reduced can only reach the cell by diffusion. As noted in *Advances in Biochemical Engineering*, volume 5. Jack and Zajic found that "cells lying deeper than 0.35 mm inside the polyacrylamid gel were being limited by oxygen deprivation." According to the "Nature" article mentioned above, an alternate approach of immobilizing cells on collagen is by the formation of a stable network of multiple ionic linkages, hydrogen bonds and Van der Walls interreactions which successfully immobilizes the cells on the hydroxides of titanium and zirconium by a chelation process. In addition there have been numerous other techniques discovered for immobilizing various bacteria.

As an example, refer to U.S. Pat. No. 4,138,292 issued to Chibata on Feb. 6, 1979 which teaches an enzyme or microorganism entrapped within the gel matrix of a sulfated polysaccharide in the presence of an ammonium ion, a metal ion, a water soluble amine or a water miscible organic solvent. Also, referring to U.S. Pat. No. 4,206,259 by Rohrback et al, there are disclosed support matrices for immobilized enzymes. More specifically, the patent shows support matrices consisting of an organic-inorganic composite in which the inorganic support material is combined with an organic copolymer prepared in situ and entrapped within the pores of the organic support. The copolymer is formed by the reactions of aminopolystyrene with a sufficient excess of bifunctional monomer to provide a copolymeric product containing terminally functionalized groups capable of covalently binding the enzymes at the terminal reactive portions. In a particular example, alumina base having a particle size from 25 to 40 mesh is added to 10 millimeters of five percent weight by volume of aminopolystyrene and 0.1 M hydrochloric acid. After standing one hour, the mixture is degased and filtered and the support containing the aminopolystyrene is dried. This composite is mixed with a 1.5 percent aqueous solution of glutaraldehyde. After a setting period the remaining organic-inorganic material is washed with water. The final immobilized conjugate is then treated with a commercial glucoamylase for 16 hours while maintaining the temperature of the composite at 4° C.

From the above, it is seen that the present methods of immobilizing bacteria are quite complex. An effective or simple attachable method would be a great help. Therefore, it is an object of this invention to provide apparatus for readily attaching bacteria. Although various types of bacteria may be used to hydrolize cellulose to sugar which is then converted to alcohol, there are, of course, various types of such operatives which are superior to others. For example, the bacterium *Clostridium thermocellum* can hydrolize cellulose to sugar and sugar to alcohol in one step, and research at Massachusetts Institute of Technology has resulted in a method of producing butanol by use of *Clostridum Acetobutylium*. Furthermore, Dr. Wang at MIT has reported that special strains of two bacteria produced by genetic mutation produce ethanol from cellulose and are tolerant to alcohol. Unfortunately, these particular bacteria can be used only with an inorganic support such as ceramic. Such bacteria would attack a support of wood or certain other organic materials.

U.S. Pat. Nos. 3,983,000, 4,071,409, 4,149,936, 4,149,937, 4,153,510 by Messing describe methods of attaching microbes to glass. Other, particularly suitable organisms include certain aerobic species of Pseudomonas from the family Pseudomonadaceae, certain endospore forming species of Clostridium from the family Bacillaceae, certain species of Actinomycetaes and Streptomyces from the family Streptomycetaceae. Finally perhaps the most promising is the anaerobic rod *Zymomonas mobilis* (*Z. mobilis*) from the family Vibrionaceae.

As has been mentioned, ethanol is a very useful alternate liquid transportion fuel which can either be blended with gasoline (gasohol) to extend present supplies or used directly by modifying the internal combustion engine. As mentioned heretofore, *Z. mobilis* has been found to be particularly effective in the production of ethanol. In comparing the kinetics of alcohol production with an anaerobic bacterium such as *Zymomonas mobilis* and a yeast *Saccharomyces cerevisiae*, the *Z. mobilis* shows favorable results. Likewise, studies and comparisons of *Z. mobilis* with yeast indicate that the glucose uptake rate is two or three times faster than yeast, and that *Z. mobilis* gave yields of up to 97% of the theoretical value. Further, genetic manipulation is simpler with bacteria such as Zymomonas species than with yeasts. This opens up the possibility of extending the range of nutrient utilization. The use of *Z. mobilis* with a specially designed fermentator should have considerable promise in minimizing the pollution problem associated with fermentation. New yeasts are being developed, however, *Kluyreromyces fragilis* ferments lactose.

The use of reaction towers and packed column reactors and other means for supporting a biomass reaction, has also received considerable attention; however, problems immediately surface whether Rashing Rings or Clyde High Area Contactors are used. For example, U.S. Pat. No. 4,127,447 issued to Griffith et. al., on Nov. 28, 1978 is concerned with the problems of a column being plugged by the build up of anaerobic microorganisms attached to the supports in an upflow packed bed. To limit this growth rate, a membrane disrupting detergent is provided in the column to lyse the dead microorganisms for making them available as nutrients for the live organisms. In addition, the growth may be restricted by limiting the availability of essential nutrients and/or by providing the presence of predatory protozoa which consume the anaerobic microorganisms.

Still another U.S. Pat. No. 3,878,301 issued to Berdelle-Hilge on Apr. 15, 1975 discloses a process of controlling the productivity of microorganisms which are held in at least one reaction bed through which nutrients flow with a short contact time. The process is characterized in that the desired productivity is obtained by deliberate quantitative and/or qualitative modification of the contact conditions between the nutrients and the microorganisms.

In a similar manner, Mr. Coulthard in his U.S. Pat. No. 3,981,803 issued Sept. 21, 1976 in which he describes an apparatus for achieving anaerobic fermentation notes the problem of the large biomass build up, but provides no solution.

However, it is suggested that restricting the growth of the biomass, or controlling the contact conditions or the nutrients or providing predatory protozoa is not the answer. Therefore, a technique for allowing uninhibited growth of the biomass for achieving the rapid conversion of sugars to alcohol is desirable; while at the same time the techniques for controlling and preventing the plugging of the reactor by the excess amounts of biomass is necessary. In recent tests by the Applicant for determining the build up of *Z. mobilis* on a Clyde High Area Contactor suspended in a solution by a string, as was mentioned earlier, it was noticed that a greater build up of bacteria occurred on the support string than on the contactor. Further experimentations showed that the build up of *Z. mobilis* was particularly great on such substrates as string, wood and netting.

Therefore, it is an object of the present invention to disclose a fermenter which encourages the growth of a selected microorganism, but in which plugging or stoppage of the fermenter by excess biomass is eliminated.

It is another object of this invention to describe a fermenter in which excess growth is controlled by mechanical or physical discharge of the biomass.

It is yet another object of this invention to describe a fermenter, wherein the excess biomass is controlled by means other than limiting the nutrients of the biomass or using predatory protozoa.

It is yet another object of this invention to describe a fermenter wherein $CO_2$ can leave without disturbing the rest of the system during the production of alcohol.

It is yet another object of this invention to describe a fermenter in which bacteria or other microorganisms easily attach to a substrate having a large area.

It is still another object of this invention to disclose a fermenter suitable for the production of alcohol and other chemicals.

It is yet another object of this invention to describe a fermenter useful in the treatment of waste water.

It is another object of this invention to provide a method for removing excess biomass from heating tubes so as to maintain efficient heat transfer. To accomplish the above mentioned objects as well as other objects which will become evident from the following detailed description, the present invention discloses apparatus which according to one embodiment comprises a container suitable for holding a selected nutrient. The container includes a port for receiving the nutrient medium, exhaust ports for discharging excess organisms and $CO_2$, and a port for removing the resulting chemical such as ethanol. A substrate comprised of a multiplicity of fibers such as string or ceramic is provided for supporting the growth of a selected microorganism such as for example Z. mobilis. The immobilizing substrate is itself supported in a desired position within the container by a support means to achieve proper flow of materials. There is also included means for physically detaching the organism from the immobilizing substrate such as by striking or ultrasonic waves. The use of Z. mobilis as the organism and glucose as the fermentable carbon source in the medium is especially useful for the production of ethanol.

DETAILED DESCRIPTION OF THE INVENTION

Figure 1:
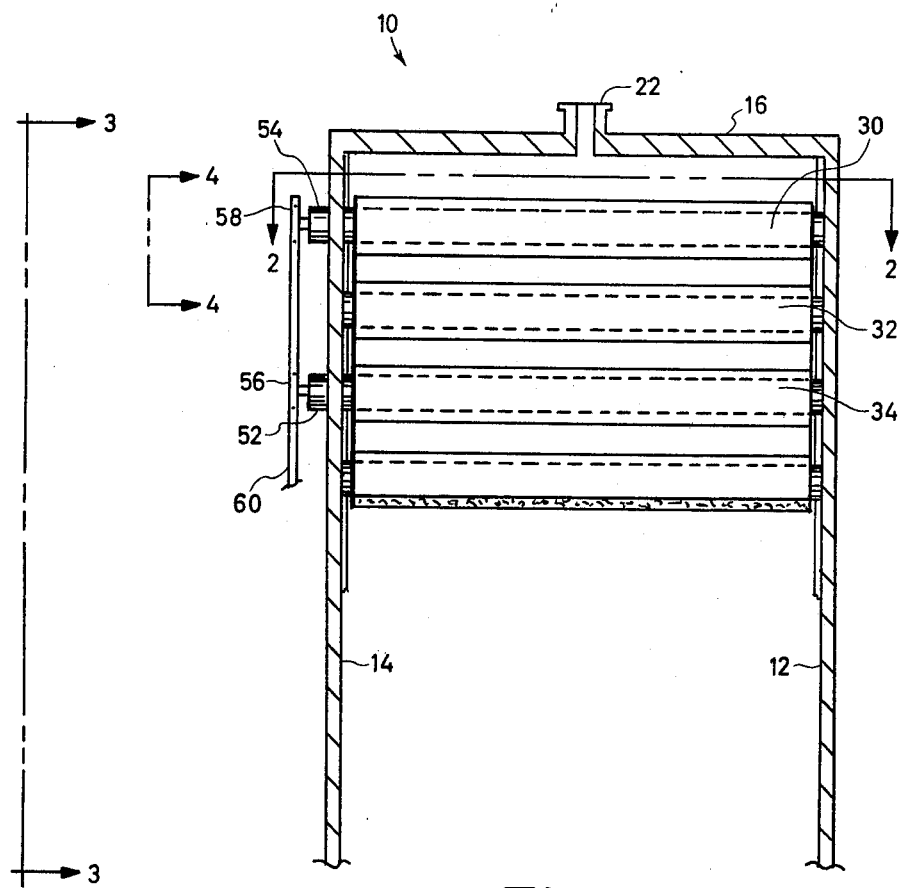
FIGS. 1, 2 and 3 are top, front and side views respectively of a fermenter which includes features of this invention.
Figure 2:
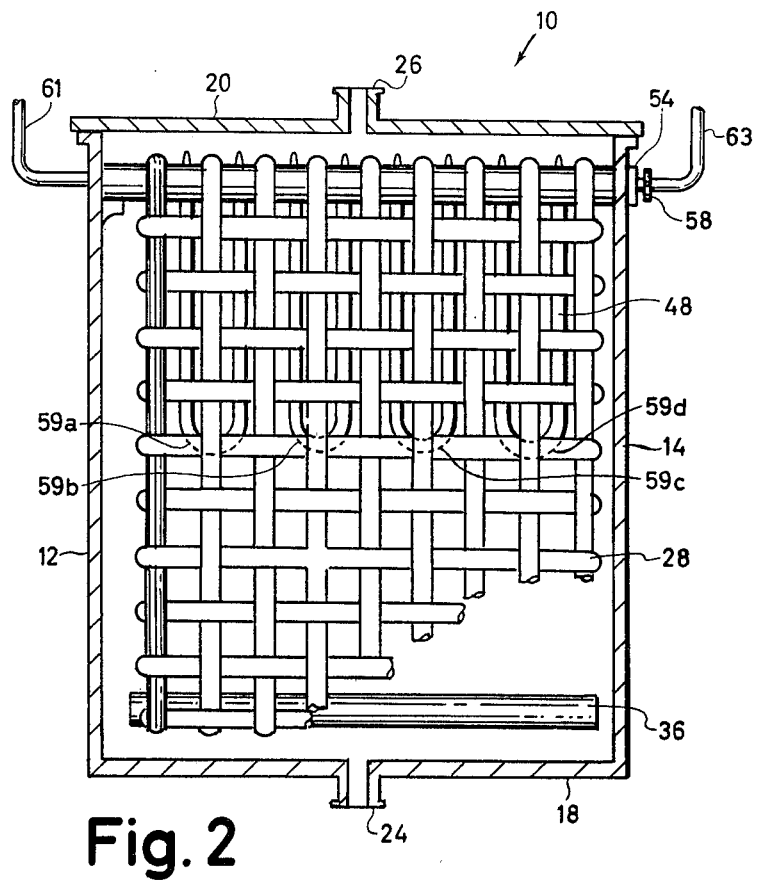
Figure 3:
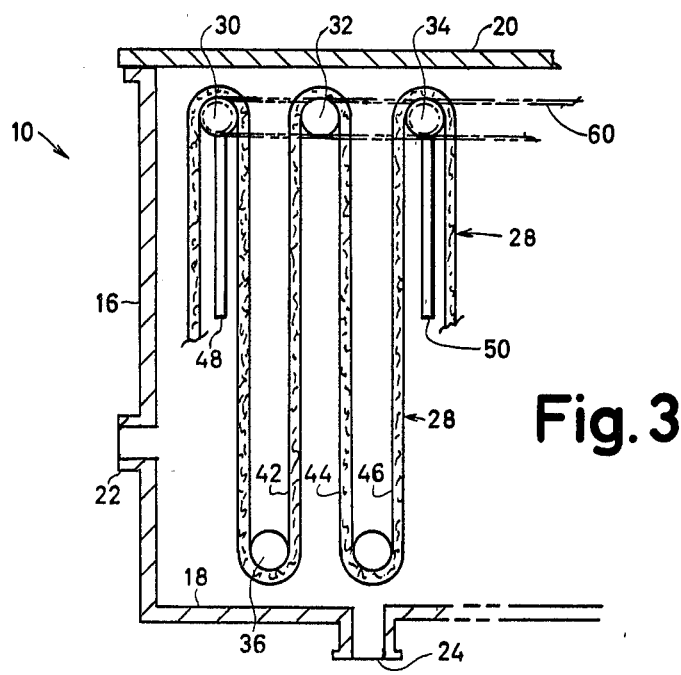
Figure 4:
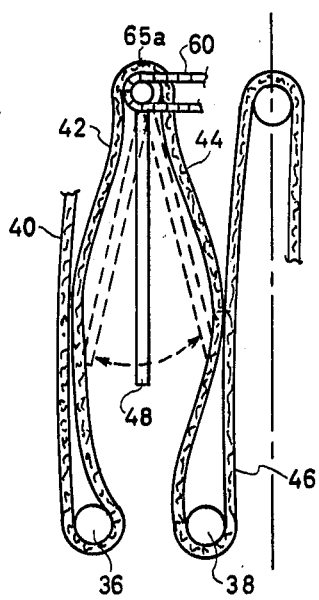
FIG. 4 shows the detailed operation of the striker bars of the fermenter of FIGS. 1, 2 and 3 for removing excess biomass.

Referring now to FIGS. 1, 2 and 3 there is shown top, front and side views respectively of a string fermenter incorporating the features of this invention. It will become obvious from the discussion of this string fermenter, that biomass or bacteria are free to grow at an uninhibited rate while at the same time any $CO_2$ by-product is readily removed from the fermenter. As shown, there is a container 10 having side panels 12 and 14, a front 16, a rear panel (not shown) and bottom panel 18. There is also shown a removable top or access panel 20. As will be discussed hereinafter, there is also included a nutrient entry port 22 and an excess biomass exit port 24. According to the embodiment shown in FIGS. 1, 2 and 3 of this invention, container 10 includes a webbing 28 supported at an upper position by rollers 30, 32, and 34 which rollers are supported by side panels 12 and 14. Also shown are lower spacer bars 36 and 38 which hang between and are supported by webbing layers 40, 42, 44 and 46. Spacer bars 36 and 38 can be of any suitable diameter, but $\frac{1}{4}''$ rods have been found effective. As can be more clearly seen in the front and side views of FIGS. 2 and 3 respectively, alternate top roller supports such as roller bars 30 and 34 include striker bars 48 and 50 securely connected to roller bars 30 and 34. Also, as can more clearly be seen in the top view of FIG. 1 and the front view 23, a pivot shaft 52 and 54 of roller bars 30 and 34 extend through side panel 14. Each of these extensions has attached thereto a spur gear such as is shown at 56 and 58. As shown in FIG. 3, a connecting chain 60 is connected around and meshes with the spur gears 56 and 58. Thus, referring now to FIG. 4, it will be appreciated that by moving drive chain 60 back and forth, striker bar 48 is rotated such it strikes layers 42 and 44 of webbing 28 which in turn is moved so that these layers strike layers 40 and 46 of webbing 28. It will be appreciated, of course, that spacing bars 36 and 38 are not attached, and therefore are free to move back and forth, or up and down as determined by webbing 28. As will be discussed hereinafter, the use of the striking bars 48 and 50 results in any excess biomass which may have accumulated on the webbing to be dislodged such that it can be discharged through exhaust port 24.

In addition, gentle mixing can be accomplished with the striker bars. Further since the fibers are much lighter than columns of Raschig Rings such as was discussed in the background of this invention, the fermenter of this invention could be used to ferment sugar being transported by a ship. Referring again to FIG. 2, the striker bars and the support rollers may be hollow and the fermenter includes connecting ends 59a, 59b, 59c and 59d, input tubing 61, and output tubing 63 (shown in dashed lines). Such an arrangement allows warm water to be circulated through the striker bars to help maintain the nutrient solution at a desired temperature.

Although the present embodiment shows the use of a webbing 28 connected between the support rollers and the spacer bars, it will be appreciated that in addition to webbing, a series of strings or fibers could, of course, be used. It will also be appreciated that the webbing 28 or in an embodiment using fibers, such webbing or fibers may be made of any suitable material such as cotton, polyester, orlon, nylon, rayon, acetate, wool, polypropylene or any combination of such materials. Although the above mentioned materials are preferred in the conversion of sugar to alcohol, in certain fermenters which directly convert organic material such as corn stalks to alcohol by means of a simultaneous biological process or the use of a bacteria such as clostridium, species organic webbing or fibers will not be satisfactory since the bacteria would also operate on such fibers. In such situations, fibers or webbing of ceramic or fiberglass is preferred. The DuPont Company has organic aramid fibers called Nomex and Kevlar. Several companies have ceramic fibers. Carborundum has Fiberfrax, 3 M has Nextel, Celanese has Celiox, Newtex Industries has Zetex, Amatex has Zetex, and Armco has Refrasil. Webbing can preferably be about one quarter inch or less apart and made of strings about one-eighth inch in diameter or less. A DuPont plastic webbing Vestar has been found to be particularly effective and cheesecloth is a good cotton webbing. Also as shown in FIG. 2, projections 65a through 65b may be attached to the top support bars to prevent the webbing from slipping.

Figure 6:
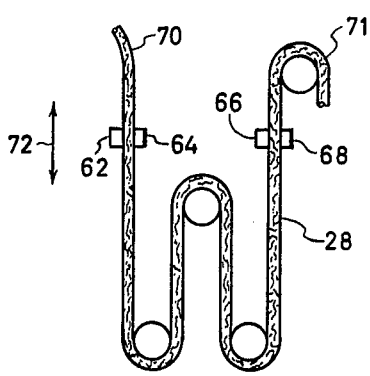
FIGS. 6 and 7 shows an alternate embodiment for scrapping excess biomass or organisms from the strong substrate.
Figure 7:
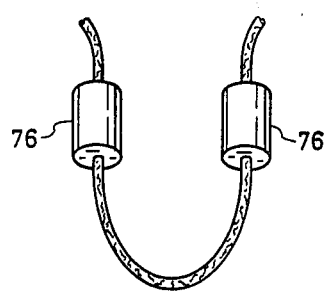
Figure 5:
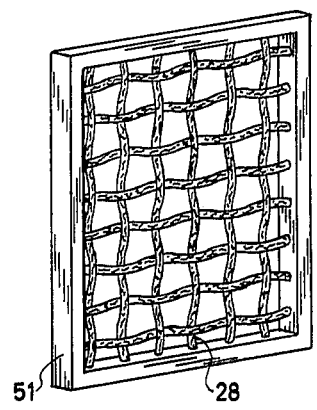
FIG. 5 shows an alternate embodiment wherein the webbing is mounted in a frame.

Alternately as shown in FIG. 5, rather than using a continuous web as was discussed heretofore, webbing 28 may be mounted in a frame 51 of any suitable material including wood, ceramic or metal. Referring now to FIG. 6, there is shown an alternate way of physically removing the excess biomass from webbing 28. As shown, in this embodiment scraper bars 62, 64, 66 and 68 are supported by side panels 12 and 14 at a spacing which is substantially the same as the thickness of the webbing 28. Portion 70 of the webbing 28 is shown extending outside of the fermenter such that by moving the webbing 28 in either direction as indicated by arrow 72, any excess biomass will be scraped off of the webbing by scraper bars 62 through 68 where it will collect at the bottom of the fermenter on bottom 18 such that it can be exhausted through exhaust port 24. Likewise, referring to FIG. 7 if individual strings are used rather than a webbing, string or fiber scrapers 74 and 76 may be used such that the fibers run through scrapers 74 and 76 such that any excess biomass adhering thereto can be scraped off of the fibers and exhausted through exhaust port 24. A continuous belt of webbing can be moved slowly through the solution.

It will also be appreciated, of course, that other means for physcially removing the organisms from the substrate could be used including ultrasonic waves.

Figure 8:
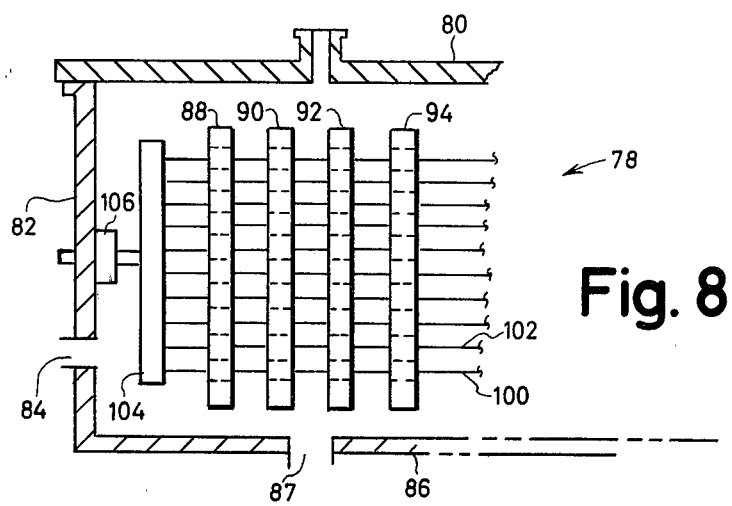
FIG. 8 shows a side view of an embodiment of this invention having wood panels as substrates.
Figure 9:
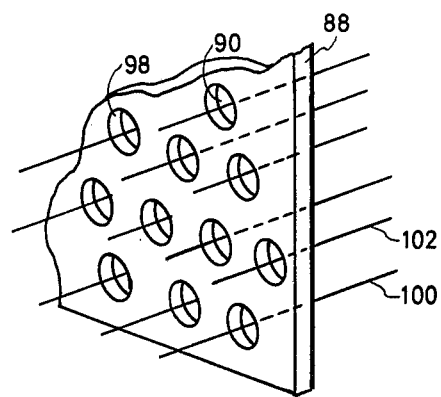
FIG. 9 shows details of the means for physically detaching biomass from the fermenter of FIG. 8.

In addition to string fermenters, it has been found that biomass or bacteria also attach readily to wooden supports. To this end, there is shown a wood fermenter generally at 78 in FIG. 8. As shown, there is a top panel 80, a front panel having a nutrient input port 84, and a bottom panel 86 having an excess biomass exhaust port 87. According to this embodiment and as is more readily seen in FIG. 9, a series of wooden panels 88, 98, 92 and 94 are supported in the fermenter 78. Each of the panels is illustrated with a series of holes as indicated by 96 and 98 in FIG. 9, although it will be appreciated that such holes are not necessary. However, in an embodiment using holes, a wire such as 100 and 102 is passed through each of the holes as is clearly shown in FIGS. 8 and 9. The wires such as 100 and 102 are supported on the front end by support structure 104 and by a second support panel at the rear side (not shown).

Support structure 104 is itself in turn supported by a cam means 106 such that the wires through the holes can be moved so that they come in contact with the holes in each of the panels and thereby remove the excess biomass.

Thus, there have been described to this point embodiments of string and/or wood fermenters which allow the uninhibited growth of biomass, provide easy access for $CO_2$ escape while at the same time providing means such that the excess biomass can be removed when necessary without inhibiting its growth or providing predatory protozoa, or closing down the system by moving $CO_2$ through to clean out excess biomass.

In operation, it is first necessary in running a fermenter to prepare a culture such as a sugar nutrient solution by sterilizing, inoculating and incubating the nutrients. The sugar nutrient may include such sugars as pentoses, hexoses, xyloses, glucose and perhaps galactose. This is especially true in the case of alcohol. This nutrient solution depending upon the type of bacteria to be grown, may for example consist of glucose, yeast $KH_2PO_4$, $(NH_4)_2SO_4$, and $MgSO_4$ as clearly described and understood by those skilled in the art. The sugar solution may, of course, be obtained by the hydrolysis of a suitable organic material such as corn stalks. A suitable organism for the intended purpose and which is compatible with the selected nutrient is then selected. Particularly, an organism may, for example, be selected from a group consisting of species in the genera of Zymomonas, Pseudomonas, Clostridium, Streptomyces, Saccharomyces, and Kluyreromyces. The selected bacteria such as the Zymomonas (*Z. mobilis*) is then transferred in any suitable manner well known by those skilled in the art and is incubated at a suitable temperature and placed in the sugar solution. In the case of *Z. mobilis* a suitable temperature is between 30 and 35 degrees centigrade. The culture then will start a rapid uninhibited growth attach to the fiber web and convert the sugar to ethanol. However, because of the uninhibited growth of the biomass, after approximately ten (10) days to two (2) weeks, the fermenter may become clogged such that free flow of the sugar solution and the $CO_2$ and the removal of alcohol is no longer possible. In that event, excess biomass can be readily removed by operation of the means for physically detaching the biomass as discussed heretofore. For example, in the case of the embodiments shown in FIGS. 1, 2 and 3, striker bars 58 and 50 are simply rotated by means of chain 60 to knock loose the biomass. In the event a wood fermenter such as that shown in FIGS. 8 and 9 has been used, rotation of cam means 106 results in movement of the wires 100 and 102 which pass through the holes of the wood panels and strikes the edge of the holes thereby removing the excess biomass. Although it has been found that *Z. mobilis* is particularly useful for converting organic materials to ethanol, it will be appreciated that other bacteria can be used. In addition, rather than alcohol, it is also possible by selection of the proper bacteria and nutrient solution that other chemicals can be obtained. For example, the use of bacteria Propionibacterium acidi propionici can generate Propionic and acetic acid at less than one fourth of the present manufacturing costs. In addition, Pseudomonas species may be attached and can convert 2-4D to $CO_2$ and water. This process is clearly described in an article by Pierce and Kidd in the July 23, 1980 *Chemical Week* magazine, page 39.

Although it has been found that the string and wood fermenter as discussed above do provide large areas for the attachment of the bacteria, it is possible to create a higher contact area on even the string or wood by the use of a high area alumina applied to the string or wood. Use of such high area alumina is described in a paper entitled "Dispal M, a Unique, New and Versatile Alumina for the Ceramic Industry" by Robert Butler of Continental Oil Company in SAE paper 730276 presented at the American Ceramics Society, Nov. 2, 1971. Mr. Butler recommends heating to 900° F., but we have found that a lower temperature results in a more positive charge which attracts negative bacteria better.

A white powder of hi-area colloidal alumina identified as Baymal and provided by Du Pont is suitable for such coating. Each particle of the powder consists of a porous aggregated mass of submicroscopic fibrous crystals or "fibrils" of boehmite alumina (AlOOH). A coating of this hi-area alumina is especially effective when supplied with a positive charge such that particles of negatively charged materials are attracted. A coating of terra sigillata can be applied.

Thus, although the present invention has been described with respect to specific methods and apparatus for providing a horizontal fermenter, it is not intended that such specific references be considered limitations upon the scope of this invention except insofar as is set forth in the following claims.

What is claimed is:

1. A fermenter for allowing the uninhibited growth of an organism suitable for converting a selected nutrient medium into a selected chemical comprising:
    a nutrient medium;
    a container for containing said nutrient medium, said container including a port for receiving said nutrient medium, exhaust ports for discharging a flow of excess organisms, and $CO_2$, and a port for removing said selected chemical;

a support substrate, said substrate comprising a multiplicity of fibers for supporting and having attached thereto said selected organisms;

means for supporting said substrate within said container; and means for physically detaching said organisms from said support substrate.

2. The fermenter of claim 1 wherein said nutrient medium is selected from the group consisting of glucose, fructose, xylose, pentose galactose, and lactose.

3. The fermenter of claims 1 or 2 wherein said organism is selected from a group consisting of species in the genera of Zymomonas, Pseudomonas, Clostridium, Streptomyces, Saccharomyces, and Kloyreromyces.

4. The fermenter of claim 1 wherein said multiplicity of fibers are in the form of a webbing.

5. The fermenter of claim 1 wherein said fibers are ceramic.

6. The fermenter of claim 5 wherein said organism is a species in genera of Clostridium.

7. The fermenter of claims 1, 4 or 5 wherein said multiplicity of fibers are located in a multiplicity of vertical planes, and wherein said means for physically detaching said organisms comprise a multiplicity of parallel rollers supported in a substantially horizontal plane, said plane located adjacent said top portion of said fermenter and said rollers being free to rotate around their longitudinal axis, said rollers being supported by said container, and a multiplicity of striking bars, each bar having one end physically attached to one of said selected rollers such that said striking bars extend between said fibers in said vertical planes and readily strike said fibers in said vertical planes when said selected rollers are rotated so that said excess organisms are dislodged from said fibers.

8. The fermenter of claim 7 wherein said support means and said striker bars are hollow to provide a fluid pathway and the unattached ends of said striker bars are connected such that a liquid can be passed through said striker bars to maintain said nutrient solution at a selected temperature.

9. The fermenter of claim 7 wherein said nutrient medium is glucose, said organism is a species in the genera Zymomonas and said chemical is ethanol.

10. The fermenter of claim 1 and further including means for moving said fibers, wherein said fibers are a multiplicity of individual fibers and said means for physically detaching comprises a multiplicity of collars, each collar defining an aperture having a diameter substantially the same as the diameter of said multiplicity of said fibers, such that movement of said strings through said collars scrapes off said excess organism.

11. The fermenter of claim 10 wherein said nutrient medium is glucose, said organism is a species in the genera Zymomonas, and said chemical is ethanol.

12. A fermenter for allowing the uninhibited growth of selected organisms suitable for converting a selected nutrient medium into a selected chemical comprising:

a nutrient medium;

a container for containing said nutrient medium, said container including a port for receiving said nutrient medium, exhaust ports for dislodging the flow of excess organisms and $CO_2$, and a port for removal of said selected chemical;

a support substrate, said substrate comprising a multiplicity of wooden panels for supporting and having attached thereto said selected organism, each panel defining a multiplicity of holes therethrough;

means for supporting said wooden panel; and a multiplicity of wires suspending through said holes in said wooden panels such that said wires can be moved into contact with the portion of said wood defining said holes such that said excess organisms can be scrapped off said wooden panels.

13. The fermenter of claim 12 wherein said nutrient medium is selected from the group consisting of glucose and fructose.

14. The fermenter of claims 12 or 13 wherein said selected organisms is selected from the group consisting of species in the genera of Zymomonas, Pseudomonis, Streptomyces, Saccharomyces, and Kloyreromyces.

15. The fermenter of claim 12 wherein said nutrient medium is glucose and said chemical is ethanol.

16. The fermenter of claims 1, 5 or 12 wherein said support substrate includes a coat of high area alumina.

* * * * *